United States Patent
Song et al.

(10) Patent No.: US 8,709,401 B2
(45) Date of Patent: *Apr. 29, 2014

(54) PRIMED STEM CELLS AND USES THEREOF TO TREAT INFLAMMATORY CONDITIONS IN JOINTS

(75) Inventors: Lin Song, Wayne, NJ (US); Marc Long, Denville, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/406,035

(22) Filed: Feb. 27, 2012

(65) Prior Publication Data

US 2012/0328578 A1 Dec. 27, 2012

Related U.S. Application Data

(60) Provisional application No. 61/446,647, filed on Feb. 25, 2011.

(51) Int. Cl.
*A01N 63/00* (2006.01)

(52) U.S. Cl.
USPC ........................ 424/93.7; 424/93.21

(58) Field of Classification Search
None
See application file for complete search history.

(56) References Cited

U.S. PATENT DOCUMENTS

| | | | |
|---|---|---|---|
| 5,486,359 | A | 1/1996 | Caplan et al. |
| 7,311,905 | B2 | 12/2007 | Hariri |
| 7,485,629 | B2 | 2/2009 | Marcum |
| 7,790,458 | B2 | 9/2010 | Xu et al. |
| 8,343,480 | B2 * | 1/2013 | Long et al. .............. 424/93.2 |
| 2002/0005205 | A1 | 1/2002 | Barry et al. |
| 2002/0110544 | A1 * | 8/2002 | Goldberg et al. ........... 424/93.7 |
| 2003/0031695 | A1 | 2/2003 | Kadiyala et al. |
| 2003/0032179 | A1 | 2/2003 | Hariri |
| 2004/0048372 | A1 | 3/2004 | Hariri |
| 2005/0089578 | A1 | 4/2005 | Werkmeister et al. |
| 2005/0260251 | A1 | 11/2005 | Hiltner et al. |
| 2007/0053963 | A1 | 3/2007 | Hotchkiss et al. |
| 2007/0059823 | A1 | 3/2007 | Verfaillie et al. |
| 2007/0098675 | A1 | 5/2007 | Elisseeff et al. |
| 2007/0264238 | A1 | 11/2007 | Shaw et al. |
| 2008/0131410 | A1 | 6/2008 | Hariri |
| 2008/0226595 | A1 * | 9/2008 | Edinger et al. ............ 424/85.4 |
| 2008/0248085 | A1 | 10/2008 | Mishra |
| 2008/0274157 | A1 | 11/2008 | Vunjak-Novakovic et al. |
| 2010/0172885 | A1 | 7/2010 | Pittenger et al. |

FOREIGN PATENT DOCUMENTS

WO 2005105121 A1 11/2005

OTHER PUBLICATIONS

Murphy et al., Arthritis & Rheumatism, 48(12): 3464-3474, 2003.*
Djouad et al., Nat. Rev. Rheumatol., 5:392-399, 2009.*
Blanc et al., Journal of Internal Medicine, 262:509-525, 2007.*
"Neochondrogenesis and the Role of Stem Cells: An Experimental Study in a Goat Model (E-94)", E-Poster (E-94), 5th International European Federation of National Associations of Orthopaetic Sports Traumatology (EFOST) Congress, Nov. 26-29, 2008, Turkey.
Saw, Khay-Yong, "A novel approach to Neocondrogenesis induced by Peripheral Blood Stem Cells and Hyaluronic Acid", E-Poster (E95), 5th International European Federation of National Associations of Orthopaetic Sports Traumatology (EFOST) Congress, Nov. 26-29, 2008, Turkey.
Gardner et al., "The efficacy of autologous platelet gel in pain control and blood loss in total knee arthroplasty", International Orthopaedics (2007) 31: 309-313.
Iwata et al., "Fibroblast growth factor-2 enhances functional recovery of reinnervated muscle", Muscle Nerve 34: 623-630, 2006.
Sanchez et al., "Plasma rich in growth factors to treat an articular cartilage avulsion: A case Report", Medicine & Science in Sports & Exercise, 2003.
Foster et al., "Platelet-Rich Plasma,From Basic Science to Clinical Applications", The American Journal of Sports Medicine, vol. 37, No. 11, 2009.
Alsousou J et al: "The biology of platelet-rich plasma and its application in trauma and orthopaedic surgery: a review of the literature", vol. 91, No. 8, Aug. 1, 2009, pp. 987-996, XP 009145933.
Castro-Malaspina et al., Blood, 59(5); 1046-1054, Publication date, May, 1982.
Croitoru-Lamoury et al. Human Mesenchymal Stem Cells Constitutively Express Chemokines and Chemokine Receptors That Can Be Upregulated by Cytokines, IFN-alpha, and Copaxone. J. Interferon Cytokine Res., 2007, vol. 27, pp. 53-64.
Elizaveta Kon et al: "Platelet-rich plasma: intra-articular knee injections produced favorable results on degenerative cartilage lesions", vol. 18, No. 4, Oct. 17, 2009, pp. 472-479, XP 019797696.
Mesoblast: the adult stem cell company, Announcement, 2 pages (2008).
Michael J Gardner et al: "The efficacy of autologous platelet gel in pain control and blood loss in total knee arthroplasty; an analysis of the haemoglobin, norcotic requirement and range of motion" vol. 31, No. 3, (Jul. 1, 2006), pp. 309-313, XP 019514225.
Murphy, et al., Arthritis & Rheumatism 48:3464-74 (2003).
Osteoarthritis and Cartilage, vol. 16, Supp. 4, pp. S44 and S54.
Practical Pain Management, vol. 8, Issue 1, Jan. 2008 to Feb. 2008, pp. 12-26.
Sanchez, et al., Med. Sci. Sports Exerc. 35 (10):1648-52 (2003).

(Continued)

*Primary Examiner* — Jennifer Pitrak McDonald
*Assistant Examiner* — Qing Xu
(74) *Attorney, Agent, or Firm* — Lerner, David, Littenberg, Krumholz & Mentlik, LLP (57) ABSTRACT

Disclosed are methods of treating inflammation within a synovial joint, comprising administering to the joint a composition comprising primed stem or progenitor cells in an amount effective to enhance recovery, and a pharmaceutically acceptable carrier.

20 Claims, 5 Drawing Sheets

(56) References Cited

OTHER PUBLICATIONS

Sen, et al., J. Cell. Biochem. 81:312-19 (2001).
Stem Cells and Bone Growth Factors: From Experimentation to Clinical Medicine: An ex Vivo In Vitro Study (2004) http://proceedings.jbjs.org.uk/cgi/content/abstract/87-B/SUPP_II/203-d?e.
The Adult Stem Cell, 1-41 (2001).
The American Journal of Sports Medicine 34:11, pp. 1774-1778, (originally published in 2006).
The American Journal of Sports Medicine, vol. 35, No. 2, pp. 245-251, 2007 (published online in 2006).
Understanding Stem Cells, National Academy of Sciences, The National Acadamies, National Acadmies Press, 2011.
Waymouth, C., Cell Culture Methods for Molecular and Cell Biology, vol. 1, Barnes et al., eds. (1984 New York).
Weber et al. Formation of cartilage matrix proteins by BMP-transfected murine mesenchymal stem cells encapsulated in a novel class of alginates. Biomaterials, 2002, vol. 23, pp. 2003-2013.
Wu Wei ; Chen Fulin; Liu Yanpu; Ma Qin; Mao Tianqiu: "Autologous injectable tissue-engineered cartilage by using platelet -rich plasma: experimental study in a rabbit model. " vol. 65, No. 10, (Oct. 2007), pp. 1951-1957, XP 022246768.
Ali et al. Addition of human mesenchymal stem cells & osteogenic protein-1 to demineralised bone matrix and insoluble collagenous matrix results in de novo bone formation. European Cells Materials, 2002, vol. 4, Suppl. 2, pp. 127-128.
Alsousou J et al: "The biology of platelet-rich plasma and its application in trauma and orthopaedic surgery: a review of the literature", vol. 91, No. 8, (Aug. 1, 2009), pp. 987-996, XP 009145933.
Bianco, et al., Stem Cells 19:180-92 (2001).
Bruder, et al., J. Cell Biochem. 64:278-294 (1997).
Burris, et al., Mol Endocrinol. 13:410-7 (1999).
Castro-Malaspina et al., Atherosclerosis, 56(20); 289-301 (1980).
Castro-Malaspina et al., Blood, 59(5); 1046-1054 (19820.
Castro-Malaspina et al., Myelofibrosis and Biology of Connective Tissue, 209-236 (1984).
Croitoru-Lamoury et al. Human Mesenchymal Stem Cells Constitutively Express Chemokines and Chemokine Receptors That Can Be Upregulated by Cytokines, IFN-$\alpha$, and Copaxone. J. Interferon Cytokine Res., 2007, vol. 27, pp. 53-64.
Elizaveta Kon et al: "Platelet-rich plasma: intra-articular knee injections produced favorable results on degenerative cartilage lesions" , vol. 18, No. 4, (Oct. 17, 2009), pp. 472-479, XP 019797696.
Erickson, et al., Biochem. & Biophys. Res. Comm. 290:763-9 (2002).
Eur Surg Res, 39: 199-207, 2007.
Foster, et al., Am. J. Sports Med. 37(11):2259-72 (2009).
Friedenstein, et al., J. Embryol. Exp. Morphol. 16:381-90 (1966).
Halvorsen, et al., Metabolism 50:407-413 (2001).
International Search Report Application No. PCT/US2010/056341, dated Jun. 8, 2011.
International Search Report, PCT/US09/06094, mailed Jan. 11, 2010.
Iwata, et al., Muscle & Nerve 34 (5):623-30 (2006).
Jones, et al., Arthr. Rheumat. 50:817-27 (2004).
Krampera et al. Mesenchymal stem cells for bone, cartilage, tendon and skeletal muscle repair. Bone, 2006, vol. 39, pp. 678-683.

\* cited by examiner

PRIMED STEM CELLS AND USES THEREOF TO TREAT INFLAMMATORY CONDITIONS IN JOINTS

CROSS-REFERENCE TO RELATED APPLICATION

This application claims the benefit of the filing date under 35 U.S.C. §119 (e), of U.S. Provisional Application No. 61/446,647, filed Feb. 25, 2011, the contents of which are incorporated by reference in their entirety.

BACKGROUND OF THE INVENTION

Synovial joints are the most common joints of the mammalian skeleton. They are highly evolved and movable. A typical synovial joint comprises two bone ends covered by a layer of articular cartilage. The cartilage is smooth and resilient, and facilitates low-friction movement of the bones in the joint. The bone ends and associated cartilage are surrounded by a joint capsule—a "sack" of membrane that produces synovial fluid. The capsule and fluid protect and support the cartilage and connective tissue, carrying nutrients to the articular cartilage and removing the metabolic wastes. The articular cartilage is a thin layer of hyaline cartilage on the epiphysis of the bone with a limited capacity for repair when damaged. Additionally, the natural aging process can cause the articular cartilage to degenerate somewhat, reducing its capacity to protect and cushion the bone ends. As in all synovial joints, where the facets contact each other there is a lining of cartilage lubricated by a thin layer of synovial fluid. The cartilage and synovial fluid decrease friction at the joint, extending joint life and preventing inflammation and associated pain.

Under normal conditions, the body maintains the synovial joint in a state of homeostasis through a variety of complex hormonal and mechanical feedback mechanisms. Two types of insult or injury can upset the delicate homeostatic balance. Repeated trauma or stress (slow chronic insult) to the joint during everyday use, e.g., athletic training or performance, is often the inciting cause of joint inflammation and loss of homeostasis. Initially, such stress results in only soft tissue inflammation in the form of synovitis or capsulitis (e.g., traumatic synovitis). Cartilage damage may or may not initially be present in the early stages of stress related injury or inflammation. However, the release of inflammatory mediators into the joint such as prostaglandins, cytokines, lysosomal enzymes and free radicals can lead to damage of articular cartilage and can cause cartilage degradation and can lead to development of degenerative joint disease (DJD).

A second type of insult or injury, the osteochondral defect, e.g., a chip fracture, is often associated with an acute mechanical failure or traumatic injury, e.g., an acute racing or training injury, although, such a fracture can be due to secondary complications associated with chronic DJD. In this scenario, the lesion often starts as a traumatically induced defect in the articular cartilage. This may occur as a fragmentation of the original tissue from the joint margins or other defect which compromises the surface and integrity of the articular cartilage. Exposure of the supporting subchondral bone to synovial fluid and the intermittent pressures of the synovial fluid generated by repeated joint movement (repeated stress and trauma of training or racing) can lead to progressive subchondral bone sclerosis and eventual dislodging of the chip or bone fragment. Left untreated, the resulting damage often becomes progressive and DJD results.

Joint inflammation may also arise as a consequence of a pathological condition such as rheumatoid arthritis, or non-injuriously as a mere consequence of the degeneration that is part of the natural aging process. For example, the cartilage covering the joint may deteriorate and start to fray. The fraying process may cause pieces of cartilage to break free, and the previously smooth surfaces may become rough. Moreover, the nerves associated with the joint become irritated and inflamed, causing severe pain and restricting movement of the joint.

Once compromised, the damage to articular cartilage is usually permanent. In general, once damaged, therapy is normally directed at limiting or reducing joint inflammation, limiting the release of inflammatory mediators, removal of the inciting cause (e.g., the chip) and replacement of synovial fluid components. These measures are combined with a period of rest to allow for healing and fibrocartilage deposition at the affected area. The long term therapeutic objective is directed at slowing the progression of degenerative processes and controlling the clinical signs of DJD. Prevention is often aimed at limiting joint inflammation before damage to cartilage occurs and in providing proper nutritional support.

Besides cartilage tissue, other tissues release inflammatory cytokines upon injury. Such tissue includes muscles, ligament, tendon, etc. Studies have shown release of inflammatory cytokines not just when these tissues are injured, but also long after the injury.

Clinically, joint inflammation is associated with joint stiffness, pain, weakness, and sometimes joint fatigue. Uniformly, the joint is tender and swollen, and often erythematous. In the United States alone, millions of patients suffer from joint inflammation. Afflicted individuals are frequently disabled, and the costs of medical care for patients suffering from such disorders are significant. While numerous means are available for treatment of joint inflammation, and new treatments continue to become available, none of these is as safe and effective as could be desired. There remains a need for new approaches and better methods to control joint inflammation.

SUMMARY OF THE INVENTION

An aspect of the present invention is directed to a method for treating or preventing inflammation or inflammatory conditions in synovial joints of mammals such as humans. The method entails, subsequent to isolation of the stem cells from a biological solution (such as blood, bone marrow and adipose tissue), and/or expansion in culture, exposing allogeneic or autologous stem or progenitor cells (such as embryonic or adult stem cells) to culture conditions including at least one active agent that mimic the inflammatory environment of the synovial joint. As a result of this exposure, the cells become conditioned or "primed" for purposes of exhibiting enhanced anti-inflammatory effects in vivo. Once primed, the cells may be cryopreserved or formulated for immediate use. The primed cells are administered to the inflamed synovial joint, preferably formulated in a composition with a pharmaceutically acceptable carrier.

In some embodiments, the cells are primed after their last passage/expansion step. Priming may be repeated. Thus, in some embodiments, the cells are primed after one, several, or each preceding passage/expansion step.

The primed cells may be administered to treat mammals including humans suffering from arthritic conditions including, for example, osteoarthritis and rheumatoid arthritis, to relieve joint pain, manage joint disease and degeneration, and to regenerate tissue that has been damaged as a result of an arthritic condition.

In some embodiments, the administration of the primed stem or progenitor cells is conducted in an office-based site. In other embodiments, the method is conducted during the course of or as an adjunct to surgery to treat or prevent inflammation of the synovial joint. Typically, the administration of the composition is the penultimate or last step in a surgical procedure, preferably an endoscopic, arthroscopic, or mini-open procedure, or prior to closure of the surgical incision. The administration may be part of the lavage step executed at the end of the surgery. The administration may be directly into the joint space or the area directly surrounding the joint, such as the synovial fluid of the knee for example.

Another aspect of the present invention is directed to a composition containing the primed allogeneic or autologous embryonic, adult stem cells, or progenitor cells, and a pharmaceutically acceptable carrier. The inventive compositions may further contain other therapeutic cells and/or agents, such as growth factors, as well as inert ingredients, such as gelling agents, hydrophilic agents, surfactants and phospholipids. The carrier may comprise elements naturally present in the synovial fluid, such as hyaluronans, glucosamine, chondroitin sulfate, aggrecans, and collagen. Thus, it may be used as a substitute for or complement to the synovial joint fluid.

The compositions and methods of the present invention may provide for prevention or expedited alleviation or recovery from joint inflammation in several ways. Even unprimed stem or progenitor cells are known to be beneficial in the context of anti-inflammatory activity in that they secrete soluble trophic factors (e.g., vascular endothelial-derived growth factor, and insulin-like growth factor-1 (IGF-1) and signals which in turn enable, accelerate, and/or enhance a positive biological process that benefits the recovery of the joint. These soluble factors may also play a chemotactic role in attracting circulating cells in the joint or in the vicinity of the joint. These properties are enhanced in primed stem cells. As shown in the working examples, primed stem or progenitor cells may upregulate inflammatory modulators such as PGE2 and down-regulate pro-inflammatory cytokines such as TNF-α.

In addition to enhanced secretion of anti-inflammatory trophic factors and chemotactic activity, and/or down-regulation of pro-inflammatory cytokines, the stem or progenitor cells differentiate into desired tissue (such as cartilaginous tissue or synoviocytes) and become incorporated into host tissues. Collectively, these properties aid in tissue regeneration, repair, stabilization, alleviation or prevention of further structural (e.g., cartilage) degeneration, lubrication, and pain reduction. Without intending to be bound by any particular theory of operation, Applicants believe that by exposing the stem or progenitor cells to the inflamed environment beforehand, they are better adapted to and have longer survival in the inflamed environment and exhibit these therapeutic activities faster in vivo, than their unprimed counterparts.

DETAILED DESCRIPTION

Stem cells for use in the present invention may be autologous (i.e., obtained from the same individual to whom the primed stem cells are to be administered) or allogeneic (obtained from the same species, e.g., human). Autologous stems cells offer the advantage of not causing immunorejection. However, allogeneic cells when carefully selected and properly manipulated can be immune-privileged and not elicit immunorejection. Allogeneic stem cells derived from bone marrow have been shown not to elicit immunorejection when injected in the joint to treat osteoarthritis. See, Murphy, et al., Arthritis & Rheumatism 48:3464-74 (2003).

Broadly, the stem cells useful in the present invention include cells derived from any stem cell source, such as umbilical cord blood, peripheral blood, fetal liver, placenta, adipose tissue, synovial fluid, and bone marrow. These samples may be fresh, frozen, or refrigerated. Methods of freezing cells are well known in the art. Thus, not only are embryonic stem cells suitable for use in the present invention but a variety of non-embryonic stem cells as well, including adult stem cells, and embryonic-like stem cells, such as those isolated from placenta, umbilical cord or umbilical cord blood. Adult stem cells offer the advantage that since they are naturally quiescent unless stimulated by a signal, they do not have to be kept from differentiating.

The stem cells of the invention may be pluripotent, which as used herein means that the cells are capable of differentiating into tissues of all three germ layers mesoderm, endoderm, and ectoderm. In addition, they are self-renewing, and can remain dormant or quiescent within tissue. Stem cells of the present invention may thus be referred to as "Pluripotent adult stem cells" (PPASCs). PPASCs are present in and can be isolated from a number of relatively accessible tissues, including bone marrow, blood, and placenta. PPASCs may be isolated, maintained and expanded in culture according to procedures known in the art. See, e.g., U.S. Patent Application Publication No. 20050260251.

The stem cells of the present invention may also be multipotent, which as used herein, refers to stem cells that are capable of differentiating into tissues of multiple origins but not all three germ layers. Multipotent stem cells are obtainable from skeletal muscle, fat, synovium, periosteum, bone, skin, and musculo-skeletal tissues, including ligament, tendon, cartilage and meniscus.

Adipose tissue offers a source of multipotent stromal or adult stem cells that may be suitable for use in the present invention. It has been demonstrated that human adipose tissue-derived stem cells can differentiate along the adipocyte, chondrocyte, and osteoblast lineage pathway. See, e.g., Erickson, et al., Biochem. & Biophys. Res. Comm. 290:763-9 (2002).

Adipose tissue is readily accessible and abundant in many individuals. Adipocytes can be harvested by liposuction on an outpatient basis. This is a relatively non-invasive procedure with cosmetic effects that are acceptable to the vast majority of patients. By "adipose" it is meant any fat tissue. The adipose tissue may be brown or white adipose tissue, derived from subcutaneous, omental/visceral, mammary, gonadal, or other adipose tissue site. Preferably, the adipose is subcutaneous white adipose tissue. Such cells may comprise a primary cell culture or an immortalized cell line. Adipose tissue offers many practical advantages for tissue engineering applications. First, it is abundant. Second, it is accessible to harvest methods with minimal risk to the patient. Third, it is replenishable. While stromal cells represent less than 0.01% of the bone marrow's nucleated cell population, there are up to $8.6 \times 10^4$ stem cells per gram of adipose tissue [Sen, et al., J. Cell. Biochem. 81:312-19 (2001)]. Ex vivo expansion over 2 to 4 weeks yields up to 500 million stem cells from 0.5 kilograms of adipose tissue. These cells can be used immediately or cryopreserved for future autologous or allogeneic applications.

Adipose tissue-derived stem or stromal cells may be isolated and expanded in accordance with standard techniques in the art. See, e.g., Burris, et al., Mol Endocrinol. 13:410-7 (1999). Adipose tissue-derived stem cells are obtained from minced human adipose tissue by collagenase digestion and differential centrifugation according to known techniques. See, e.g., Halvorsen, et al., Metabolism 50:407-413 (2001).

Adipose tissue from a variety of sources may be processed to produce stem cells for the generation of a cell possessing at least one genotypic or phenotypic characteristic of a chondrocyte for repair of an articular cartilage defect. The adipose tissue may be from subcutaneous, breast or perirenal sites. Preferably the adipose tissue is subcutaneous. Liposuction surgery or penniculectomy may provide subcutaneous adipose tissue.

Mesenchymal stem cells or bone marrow stromal cells may also be suitable for use in the present invention. The mesenchymal stem cells may be obtained (e.g., from bone marrow aspirate) and expanded in culture by means known to those skilled in the art. See, e.g., U.S. Patent Application Publication No. 20020005205. Bone marrow stromal cells are mixed-cell populations that generate bone, cartilage, fat, fibrous connective tissue and the reticular network that supports blood cell formation. See, e.g., Friedenstein, et al., J. Embryol. Exp. Morphol. 16:381-90 (1966). Bone marrow stromal cells have many features that distinguish them from hematopoietic stem cells (HSCs). The two cell types are easy to separate in vitro. When bone marrow is dissociated, and the mixture of cells it contains is plated at low density, the stromal cells adhere to the surface of the culture dish but the HSCs do not. Given specific in vitro conditions, bone marrow stromal cells form colonies from a single cell called the colony forming unit-F [CFU-F]. These colonies may then differentiate as adipocytes or myelosupportive stroma, a clonal assay that indicates the stem cell-like nature of stromal cells. Unlike HSCs, which do not divide in vitro (or proliferate only to a limited extent), bone marrow stromal cells can proliferate for up to 35 population doublings in vitro. See, e.g., Bruder, et al., J. Cell Biochem. 64:278-294 (1997). They grow rapidly under the influence of such mitogens as platelet-derived growth factor [PDGF], epidermal growth factor [EGF], basic fibroblast growth factor (bFGF], and insulin-like growth factor-1 [IGF-1]. See, e.g., Bianco, et al., Stem Cells 19:180-92 (2001).

Mesenchymal stem cells suitable for use in the present invention may also be obtained from synovial fluid of both healthy and arthritic individuals. See, e.g., Jones, et al., Arthr. Rheumat. 50:817-27 (2004).

Pluripotent cells suitable for use in the present invention may also be obtained from umbilical cord or umbilical cord blood.

The human placenta is yet another source of stem cells suitable for use in the present invention. For example, U.S. Pat. No. 7,311,905 and U.S. Patent Application Publication No. 20040048372 teach that the human placenta is rich in several different types of stem cells (placental stem cells), including embryonic-like stem cells. As used herein, the term "embryonic-like stem cell" refers to a cell that is not derived from the inner cell mass of a blastocyst. An embryonic-like stem cell is preferably pluripotent. The stem cells which may be obtained from the placenta also include, in addition to embryonic-like stem cells, multipotent cells, and committed progenitor cells. Embryonic-like stem cells derived from the placenta may be collected from the isolated placenta once it has been exsanguinated and perfused for a period of time sufficient to remove residual cells. As used herein, the term "placental stem cell" is derived from a post-partum perfused placenta.

Prior to priming, a large proportion of terminally differentiated cells may be removed from a stem cell source by negatively selecting differentiated cells. For example, large numbers of lineage-committed cells can be removed by selective magnetic bead separations. In some embodiments, at least about 80%, usually at least about 70% of the differentiated cells will be removed prior to culture.

The stem or progenitor cells may be primed in several ways. They may be cultured in base media that contains, for example autologous or allogeneic synovial fluid from an inflamed joint. Typically, the concentration of the synovial fluid ranges from about 1% to about 90% and in some embodiments from about 10% to about 50% v/v, based on the total volume of the media. In these embodiments, particularly when autologous synovial fluid is used, priming may be conducted at the point of care. Alternatively, the cells for use in the present invention may be cultured in an environment that mimics that inflammatory environment. This may be accomplished by culturing the cells in medium containing one or more pro-inflammatory cytokines, such as interferon-γ, TNF-α, IL-1 (inclusive of IL-1α, β, and IL-1 receptor antagonist), IL-4, IL-6, IL-7, IL-8, MCP-1 and MIP-1β, as well as vascular adhesion molecules. In some embodiments, the medium contains at least one or a cocktail of at least two pro-inflammatory cytokines, selected from interferon-γ, TNF-α, and IL-1β. In a further embodiment, the cells are primed by culturing them in medium containing one or more enzymes, typically proteolytic enzymes, commonly present (in greater amounts) in inflamed joints. Such proteolytic enzymes include aggrecanase, collagenase, caspases, and MMPs (matrix metalloproteinases). Inflammatory conditions may also be created in vitro by incorporating at least one pro-inflammatory cytokine and at least one proteolytic enzyme, and preferably a cocktail of cytokines and/or enzymes, into a culture medium. Representative cocktails include at least one cytokine e.g., IL-1β, and at least one enzyme e.g., a metalloproteinase (e.g., MMP-1, MMP-2, MMP-3), a collagenase, and an aggreganase (e.g., IL-1β and MMP-1, IL-1β and MMP-2, IL-1β and MMP-3, IL-1β and a collagenase, IL-1β and an aggreganase.

The synovial fluid, or at least one cytokine and/or enzyme combinations may be added to a base nutritive medium to provide a culture medium suitable for priming the stem cells. Any nutritive medium suitable for the culture of mammalian cells, particularly stem cells, may be used, for example, Stemline™ (Sigma-Aldrich, MO). The final concentration of these pro-inflammatory cytokines in the nutritive or base medium generally ranges from 1 femtogram/ml to 1 picogram/ml to 1 nanogram/ml to 1 milligram/ml. In some embodiments, the concentration of any one of the cytokines can be 1 pg/ml, 5 pg/ml, 10 pg/ml, 15 pg/ml, 20 pg/ml, 25 pg/ml, 30 pg/ml, 35 pg/ml, 40 pg/ml, 45 pg/ml, 50 pg/ml, 55 pg/ml, 60 pg/ml, 65 pg/ml, 70 pg/ml, 75 pg/ml, 80 pg/ml, 85 pg/ml, 90 pg/ml, 95 pg/ml, 100 pg/ml, 110 pg/ml, 120 pg/ml, 130 pg/ml, 140 pg/ml, 150 pg/ml, 160 pg/ml, 170 pg/ml, 180 pg/ml, 190 pg/ml, 200 pg/ml, 210 pg/ml, 220 pg/ml, 230 pg/ml, 240 pg/ml, 250 pg/ml, 260 pg/ml, 270 pg/ml, 280 pg/ml, 290 pg/ml, 300 pg/ml, 310 pg/ml, 320 pg/ml, 330 pg/ml, 340 pg/ml, 350 pg/ml, 360 pg/ml, 370 pg/ml, 380 pg/ml, 390 pg/ml, 400 pg/ml, 410 pg/ml, 420 pg/ml, 430 pg/ml, 440 pg/ml, 450 pg/ml, 460 pg/ml, 470 pg/ml, 480 pg/ml, 490 pg/ml, 500 pg/ml, 510 pg/ml, 520 pg/ml, 530 pg/ml, 540 pg/ml, 550 pg/ml, 560 pg/ml, 570 pg/ml, 580 pg/ml, 590 pg/ml, 600 pg/ml, 610 pg/ml, 620 pg/ml, 630 pg/ml, 640 pg/ml, 650 pg/ml, 660 pg/ml, 670 pg/ml, 680 pg/ml, 690 pg/ml, 700 pg/ml, 710 pg/ml, 720 pg/ml, 730 pg/ml, 740 pg/ml, 750 pg/ml, 760 pg/ml, 770 pg/ml, 780 pg/ml, 790 pg/ml, 800 pg/ml, 810 pg/ml, 820 pg/ml, 830 pg/ml, 840 pg/ml, 850 pg/ml, 860 pg/ml, 870 pg/ml, 880 pg/ml, 890 pg/ml, 900 pg/ml, 910 pg/ml, 920 pg/ml, 930 pg/ml, 940 pg/ml, 950 pg/ml, 960 pg/ml, 970 pg/ml, 980 pg/ml, 990 pg/ml, 1 ng/ml, 1.5 ng/ml, 2 ng/ml, 2.5 ng/ml, 3 ng/ml, 3.5 ng/ml, 4 ng/ml, 4.5 ng/ml, 5 ng/ml, 6 ng/ml, 7 ng/ml, 8 ng/ml, 9 ng/ml, 10 ng/ml, 15 ng/ml, 20 ng/ml, 25 ng/ml, 30 ng/ml, 35 ng/ml, 40 ng/ml, 45 ng/ml, 50 ng/ml, 55 ng/ml, 60 ng/ml, 65 ng/ml, 70 ng/ml, 75 ng/ml, 80 ng/ml, 85 ng/ml, 90 ng/ml, 95 ng/ml, 100 ng/ml, 110 ng/ml, 120 ng/ml, 130 ng/ml, 140 ng/ml, 150 pg/ml, 160 ng/ml, 170 ng/ml, 180 ng/ml, 190 ng/ml, 200 ng/ml, 210 ng/ml, 220 ng/ml, 230 ng/ml, 240 ng/ml, 250 ng/ml, 260 ng/ml, 270 ng/ml, 280 ng/ml, 290 ng/ml, 300 ng/ml, 310 ng/ml, 320 ng/ml, 330 ng/ml, 340 ng/ml, 350 ng/ml, 360 ng/ml, 370 ng/ml, 380 ng/ml, 390 ng/ml, 400 ng/ml, 410 ng/ml, 420 ng/ml, 430 ng/ml, 440 ng/ml, 450 ng/ml, 460 ng/ml, 470 ng/ml, 480 ng/ml, 490 ng/ml, 500 ng/ml, 510 ng/ml, 520 ng/ml, 530 ng/ml, 540 ng/ml, 550 ng/ml, 560 ng/ml, 570 ng/ml, 580 ng/ml, 590 ng/ml, 600 ng/ml, 610 ng/ml, 620 ng/ml, 630 ng/ml, 640 ng/ml, 650 ng/ml, 660 ng/ml, 670 ng/ml, 680 ng/ml, 690 ng/ml, 700 ng/ml, 710 ng/ml, 720 ng/ml, 730 ng/ml, 740 ng/ml, 750 ng/ml, 760 ng/ml, 770 ng/ml, 780 ng/ml, 790 ng/ml, 800 ng/ml, 810 ng/ml, 820 ng/ml, 830 ng/ml, 840 ng/ml, 850 ng/ml, 860 ng/ml, 870 ng/ml, 880 ng/ml, 890 ng/ml, 900 ng/ml, 910 ng/ml, 920 ng/ml, 930 ng/ml, 940 ng/ml, 950 ng/ml, 960 ng/ml, 970 ng/ml, 980 ng/ml, 990 ng/ml, 1000 ng/ml, and subranges therein. In some embodiments, the concentration of the cytokine is about 1 ng/ml to about 100 ng/ml and in other embodiments, about 10 ng/ml to about 50 ng/ml. Those skilled in the art recognize that these cytokines may be concentrated and, in some instances, lyophilized before addition to the nutritive or base medium to obtain the examples of final concentrations listed above. Those skilled in the art also recognize that the mass weight added to culture will depend on the specific biological activity of the cytokine preparation. Bioassays to determine the biological potency of cytokines are well known in the art. Therefore, where the biological activity is correlated to a mass weight, then biological "units" as defined by the assay are used.

Autologous or allogeneic synovial fluid, pro-inflammatory cytokines and proteolytic enzymes aside, the medium preferably contains serum. The medium may also contain other types of cells (e.g., lymphocytes (including B-lymphocytes and T-lymphocytes) as well as one or more therapeutic agents that inhibit differentiation of stem or progenitor cells.

Methods of culturing or expanding stem cells from a stem cell source in nutritive media are well known in the art. See for example Waymouth, C., *Cell Culture Methods for Molecular and Cell Biology*, Vol. 1, Barnes et al., eds. (1984 New York). By "cell-culture" it is intended to mean the maintenance of individual cells, tissues, organ systems or whole organisms in an artificial in vitro environment. In some embodiments, cells derived from a stem cell source are placed in a culture vessel containing the nutritive medium. The medium may contain the cytokine combination, or the cytokines can be added later. Cells are then incubated with the cytokine combination at a temperature suitable for cell growth (for some embodiments about 37° C.), for at least 24 hours, at least 48 hours, at least 72 hours, at least 96 hours, or longer, e.g., about 2 weeks. Cells may be harvested in any manner known in the art including but not limited to centrifugation for collecting non-adherent cells, trypsinizing adherent cells, or scraping cells from the surface.

Cryopreservation of stem cells prior to culture or cryopreservation of the cells following priming and/or expansion may be carried out according to known methods. For example, cells may be suspended in a "freezing medium" such as, for example, culture medium further comprising 10% dimethylsulfoxide (DMSO), with or without 5-10% glycerol, at a density, for example, ranging from about $0.5 \times 10^6$ to about $4 \times 10^6$ cells/ml. The cells are dispensed into glass or plastic vials, which are then sealed and transferred to a freezing chamber of a programmable or passive freezer. The optimal rate of freezing may be determined empirically. For example, a freezing program that gives a change in temperature of −1° C./min through the heat of fusion may be used. Once vials containing the cells have reached −80° C., they are transferred to a liquid nitrogen storage area. Cryopreserved cells can be stored for a period of years.

In some embodiments, freshly isolated cells from any stem cell source may be cryopreserved to constitute a bank of cells, portions of which can be withdrawn by thawing and then used to produce the expanded cells of the invention as needed. Thawing should generally be carried out rapidly, for example, by transferring a vial from liquid nitrogen to a 37° C. water bath. The thawed contents of the vial should be immediately transferred under sterile conditions to a culture vessel containing an appropriate medium such as nutritive medium. Once in culture, the cells may be examined daily, for example, with an inverted microscope to detect cell proliferation, and subcultured as soon as they reach an appropriate density.

Priming aside, the stem or progenitor cells of the present invention may be further treated or manipulated, physically, chemically or genetically to enhance their anti-inflammatory properties. In some embodiments, the cells are "homed" so that they can preferentially target specific tissue or tissues. The treatment may include using a specific peptide, or peptides, or molecule that binds to the cells being administered, with one active segment being specific to binding to a specific tissue or specific tissues of the joint. A preferred embodiment entails treating the cells so they home onto synovial tissue. Another preferred embodiment entails treating the cells so they home onto articulating cartilage and/or fibrocartilage (meniscus) tissue.

The cells for use in the present invention may be genetically manipulated prior to use. They may be transfected with genes encoding growth factors, cytokines, or extra-cellular matrix compounds over-expression using gene therapy technologies. Examples of growth factors include BMPs (e.g., BMP-7), TGF-β, IGF1, β-FGF, and cartilage matrix oligomeric protein. Examples of cytokines include IL-1 receptor antagonist and other interleukin cytokines. Examples of extra-cellular compounds include hyaluronan and collagen.

The primed stem cells or progenitor cells are formulated into a composition including a pharmaceutically acceptable carrier for administration to the surgical area. The selection of a suitable carrier is within the skill of the ordinary artisan. Carriers may be broadly classified as aqueous-based and gel-based. Representative examples include plasma (autologous and allogeneic), serum (autologous and allogeneic), platelet rich plasma (PRP), water for injection, hyaluronan, chemically modified hyaluronan, saline, phosphate buffered saline, physiological saline, culture medium, chondroitin sulfate, glucosamine, mannosamine, proteoglycan, proteoglycan fragments, chitin, chitosan, or other polysaccharide or polymer materials, and combinations of two or more thereof.

Suitable gel and/or gel-forming substances may also be included in the composition. The gel and/or gel-forming substance may contain an adhesive material such as fibrin, collagen or a transglutaminase system, to adhere the gel or formed gel to the tissues surrounding the site of administration. Suitable gels and gel-forming substances include biologically-based polymers such as a collagen solution or fibrous suspension, hyaluronan, chemically modified hyaluronan, chitosan (hydrolysed chitin), and synthetic polymers such as a photopolymerizable end-capped block copolymer of poly(ethylene oxide) and an α-hydroxy acid. The compositions may further contain surfactants (e.g., lubricin, lipids (e.g., glycerols) and phospholipids or surface-active phospholipids (SAPL) (e.g., DPPC, PLPC, POPC, SLPC, and combinations thereof), and combinations of two or more thereof.

The compositions may further include other cells such as differentiated cells including, for example B- and T-lymphocytes, and non-cellular therapeutically beneficial agents such as growth factors (e.g., TGF-β, EGF, FGF, IGF-1, BMP-7 and OP-1, etc.), glycosaminoglycans (GAGs) (e.g., aggrecan, decorin, biglycan, fibromodulin), chemokines and cytokines (e.g., interleukins and interferons), hydrophilic compounds (e.g., polylysine, chitosan, hyaluronan) and antimicrobial agents such as antibiotics and anti-bacterial agents. Extracellular matrix molecules that bind to growth factors, e.g., heparin sulfate proteoglycans, may advantageously be added to serve as a reservoir for the factors.

Accordingly, the compositions of the present invention may be administered to inflamed synovial joints, including knee joints, hip joints, shoulder joints, elbow joints, ankle joints, tarsal and metatarsal joints, wrist joints, spine, carpal and metacarpal joints, and the temporal mandibular joint. The compositions and methods of the present invention may be used to treat acute and chronic joint inflammation. As used herein "acute inflammation" is used to refer to joint or chondral or cartilaginous or meniscal injury associated with pain for about 30 weeks or less. The term acute is thus used to differentiate such pain or inflammation from chronic disorders such as osteoarthritis or any other type of chronic disorder. A chronic disorder is generally regarded as being associated with periods of pain longer than about 30 weeks or any damage to the joint that is associated with general, age-related deterioration of the joint.

The stem or progenitor cells are administered in an amount effective to treat or prevent the inflammation. The present invention is not limited in terms of the origin or source of the joint inflammation. Joint inflammation typically arises from chronic tendinopathy, injury or trauma (e.g., acute ligamentous injuries), inflammatory autoimmune diseases (e.g., rheumatoid arthritis), osteoarthritis (OA) and/or degenerative joint disease (DJD), the natural ageing process, or surgical procedures such as total knee arthroplasty, ACL reconstruction, acute achilles tendon repair, rotator cuff repair, acute cartilage and meniscus repair.

The exact number of cells is dependent upon a variety of factors, including the age, weight, and sex of the patient, the extent and severity of the damage or injury to the joint, or of the inflammatory disease or condition affecting the joint, the degree of exudation within the joint, the joint space, and other anatomical characteristics that might influence the delivery, and the nature of the carrier. In general, effective amounts of the stem or progenitor cells for these purposes, and particularly when formulated in a liquid carrier such as autologous PRP, range generally from about $1 \times 10^4$ to about $2 \times 10^8$, preferably from about $2 \times 10^4$ to about $1.5 \times 10^8$, more preferably from about $4 \times 10^4$ to about $5 \times 10^7$, per single administration. Amounts of the stem or progenitor cells when formulated in a hydrogel (e.g., hyaluronic acid- or phospholipids-based) carrier may be about $1 \times 10^7$ per ml of carrier, per single administration. The cells are typically delivered in a volume of about 1 ml to about 10 ml, via any medically acceptable device for delivering fluids to synovial joints. In the case of hydrogel carriers, preferred volumes tend to be less, e.g., about 1 to about 6 ml, and in some embodiments about 1.5 to about 3 ml.

In general, the inflamed joint receives at least one administration of the primed stem or progenitor cells. Multiple administrations may be conducted at intervals generally ranging from about 1 to two weeks. In the context of surgery, the cells and the carrier may be administered to the joint such as by adding the cell solution into the last bag for last step lavage at the end of an arthroscopic intervention. Other embodiments entail administering the primed cells by pouring, squirting, spraying, flowing the cell composition in the joint space prior to closure of the joint. The timing of the administration during the course of a surgery is not critical, but is typically performed as the penultimate or last step prior to closure of the surgical opening. Another preferred embodiment in the context of surgery is to inject the cell composition prior to closing the joint or after the joint is closed at the end of the surgical intervention.

In the case of chronic disease such as osteoarthritis and rheumatoid arthritis, the administration of the primed cells may be repeated at intervals ranging from months to years, for example every 6 months, or on yearly basis.

The present invention will now be described in terms of the following non-limiting examples.

EXAMPLE 1

The effect of exposing cells to an inflammatory environment in vitro was evaluated using ex vivo synovium and cartilage explant models. Synovium and cartilage tissues were explanted from pig animals and exposed to IL-1β using the following protocol and groups:

DMEM/2% FBS/1% antibiotics ± IL-1β
Up to 5 days
↓
PGE2 & TNFα in medium

DMEM/10% FBS/1% antibiotics ± IL-1β
Up to 5 days
↓
PGE2 & GAG in medium

In this model, IL-1β induced PGE2 and TNFα production in synovium explants. IL-1β induced PGE2 production and GAG release in cartilage explants. Following the validation of the ex-vivo model, human mesenchymal stem cells (passage 3, commercially available from Lonza, Inc.) were added to the explants.

In synovium explants, hMSCs appeared to decrease endogenous but not IL-1β-induced production of PGE2 and to reduce IL-1β-induced TNFα production. In cartilage explants, hMSCs reduced endogenous PGE2 production but increased IL-1β induced PGE2 production while had little effect on GAG release.

Human MSCs were then primed in the presence of IL-1β at a concentration of 10 ng/ml.

Figure 1A:
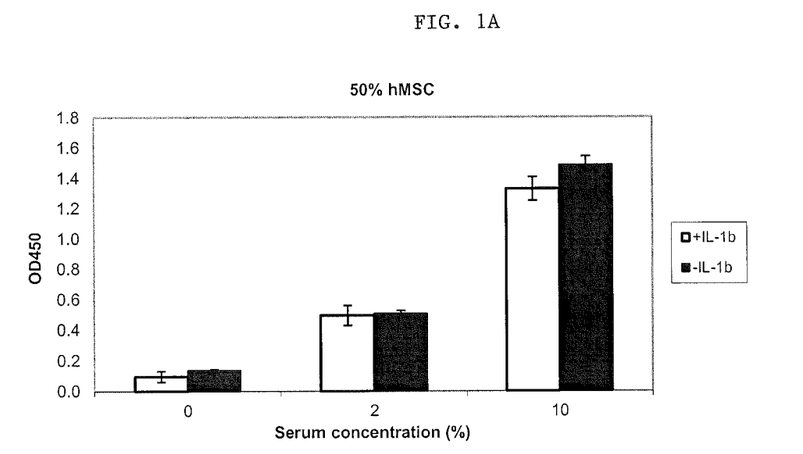
FIGS. 1A and B are bar graphs illustrating that when human mesenchymal stem cells (hMSCs) were primed in the presence of Interleukin (IL)-1β, cell proliferation was independent of IL-1β and cell density but was dependent on serum concentration.
Figure 1B:
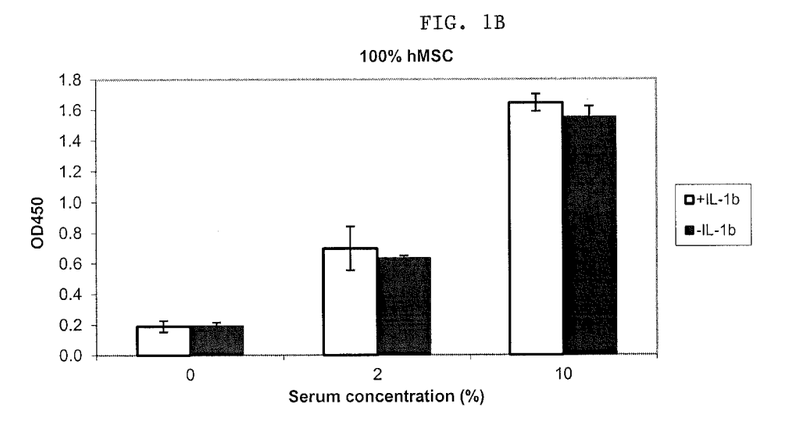

As illustrated in FIGS. 1A and B, when hMSCs were primed in the presence of IL-1β, cell proliferation was independent of IL-1β and cell density but dependent on serum concentration.

Figure 2A:
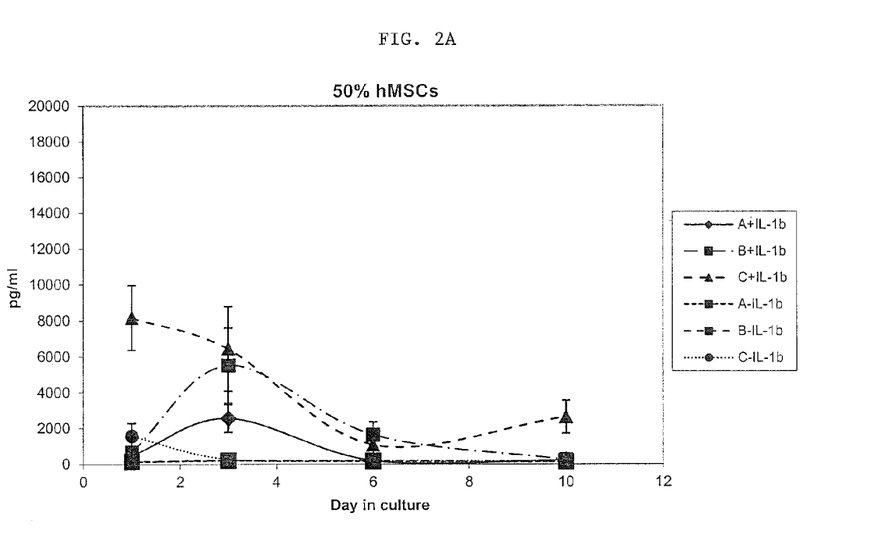
FIGS. 2A and B are graphs that illustrate that priming of hMSCs with IL-1β increased production of PGE2 (in pg/ml) compared to control, and that the effect was modulated by serum concentration, cell density and culture duration.
Figure 2B:
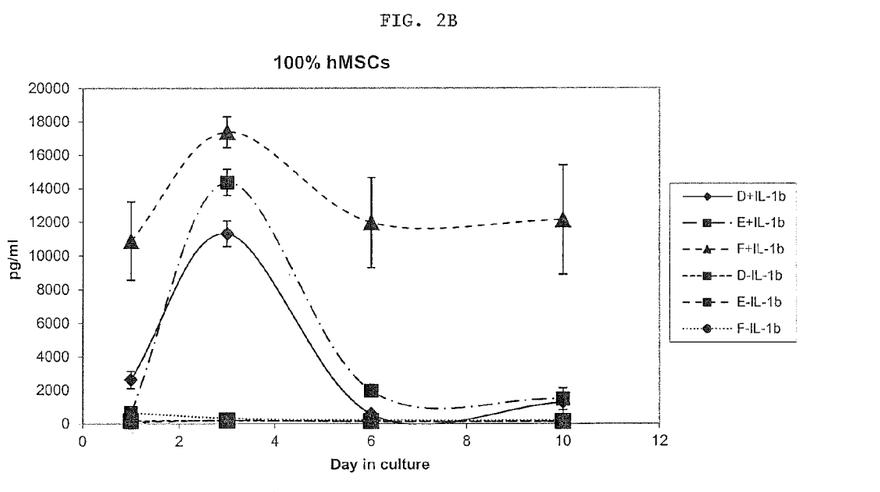

As illustrated in FIGS. 2A and B, priming of the cells with IL-1β increased PGE2 production compared to cells which had not been exposed to IL-1β prior to addition to the explants. This effect was modulated by the serum concentration, cell density and culture duration. The maximum effect was observed with the highest cell concentration, highest serum concentration and at early days in culture (3 days).

Figure 3:
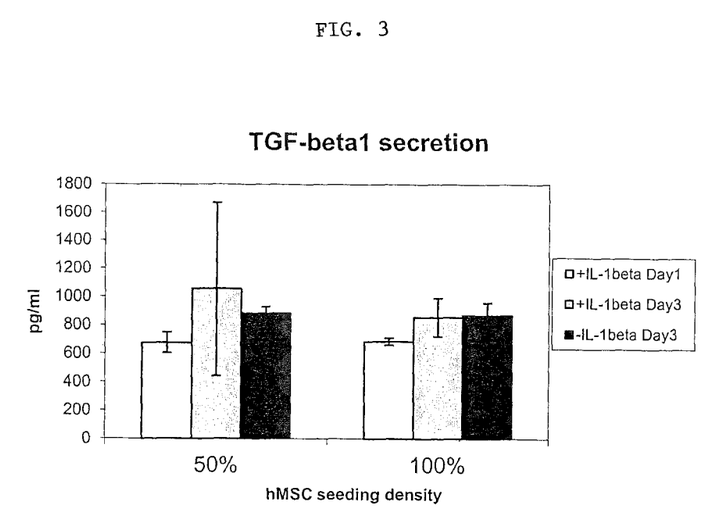
FIG. 3 is a bar graph that shows effect of priming hMSCs with IL-1β on production of TGF-β1.

As illustrated in FIG. 3, priming of the cells with IL-1β had little effect on endogenous TGF-β1 production.

Based on this ex-vivo model, human cells appeared to have modulatory effect on PGE2 and TNFα production in synovium and cartilage explants. When primed with IL-1β, these cells further enhanced the production of PGE2, while no significant effect was observed with the production of TGF-β1. These in-vitro results demonstrate that stem or progenitor cells exposed to IL-1β have a specific modulatory effect on tissue in an inflammatory environment such that they may be primed prior to their use to tailor their performance based on the environment they will be exposed to when used as therapies.

EXAMPLE 2

Male Sprague Dawley rats (191-232 grams in weight, n=15/group) were injected with 2 mg of MonoIodoAcetate (MIA) (40 µl) on day 0 on their right knees. This MIA model is an art-recognized model to evaluate OA therapies. Animals were given a single intra-articular (IA) dose of hyaluronic acid (HyA) or saline with or without stem cells one week after surgery. Animals were terminated at three weeks post surgery.
Treatment groups were as follows:

| Group | Treatment (40 µl/joint) | Cell#/knee | Priming | Carrier |
|---|---|---|---|---|
| HA | HA | — | – | — |
| Low cell+/HA | MSC | $1 \times 10^6$ | + | HA |
| Low cell−/HA | MSC | $1 \times 10^6$ | – | HA |
| High cell+/HA | MSC | $5 \times 10^6$ | + | HA |
| High cell−/HA | MSC | $5 \times 10^6$ | – | HA |
| Saline | Saline | — | – | — |
| Low cell+/saline | MSC | $1 \times 10^6$ | + | Saline |
| Low cell−/saline | MSC | $1 \times 10^6$ | – | Saline |
| Normal ctrl* | — | — | – | — |

Cells were rat bone marrow derived mesenchymal stem cells (GIBCO®) cultured and passaged at P3. Priming of the cells was conducted by incubating the cells in IL-1β for (10 ng/ml) 4 days.

Gait analysis, incapacitance (IC) testing, and knee diameter measurement were performed before MIA injection and on days 3, 7, 14, 21, 28, and 35 days post-injection. Animals were sacrificed on days 21 (n=15) for microCT and histopathologic evaluation. The timeline for treatment and evaluations is summarized below:

For standing pain, weight bearing (left vs. right) was recorded using an incapacitance meter and the following method: animals were placed in the plexiglass housing of the incapacitance meter and allowed to acclimate for approximately 2-5 minutes. The position of the animal was such that each hind paw rested on a separate force plate. The force exerted on each plate was measured until three consecutive, consistent, and positive (leaning to the left) measurements were recorded. The mean of these three readings constituted one data point. Right paw force was compared to left for each group to confirm that animals were showing pain. Difference in force (left minus right) and right paw force as a percentage of the total force exerted by both paws were determined and compared between groups, as was the percentage of the total body weight that was carried on the hind legs.

For moving pain, gait analysis was performed on the same days as incapacitance by applying ink to the ventral surface of the foot and documenting weight bearing during movement (footprints) across paper. Rear feet of rats were placed in colored ink, and black ink was applied to the dorsal side of the foot on the suspected painful leg. Rats were placed on paper and allowed to walk the full length, then removed. Gait was scored as follows: 0=Normal, equal ink staining on both feet; 1=Slight limp, toe staining evident and some heel staining for most steps. If left has very little heel staining (rat walks mainly on toes) then slightly less toe staining in MIA leg for most steps (or approximately 25% less staining on right vs. left); 2=Limping, toes only staining for all steps, no heel or posterior foot, If left has very little heel staining (rat walks mainly on toes) then significantly less toe staining in MIA leg for most steps, no carrying or dragging (or approximately 50% less staining on right vs. left); 3=Limping, toes only staining for all steps, no heel or foot pad, If left has very little heel staining (rat walks mainly on toes) then faint toe staining in MIA leg for all steps, no carrying or dragging (or approximately 75% less staining on right vs. left); and 4=Carrying leg entire time, no staining from painful leg or only minor black drag marks or smeared blue marks, no toe staining in any print (100% less staining on right vs. left)

In addition, the gait analysis footprints were analyzed digitally using Adobe Photoshop to measure the average lightness (0 [fully inked] to 255 [pure white]) in a 400×400 pixel area around each footprint. When possible, two pairs of footprints were evaluated for each animal. The inking level (value for a blank section of the page–value of the footprint area) was determined for each foot, and the right leg inking level is expressed as a percentage of the left. Values greater than 100% are considered to be 100% exactly, to provide a scale of 0 (all weight on the left leg) to 100% (even weight bearing). This percentage is then subtracted from 100% to determine the Gait Deficiency, indicating the percentage of decrease in inking.

For microCT evaluation, the right knee from each animal was scanned at a nominal resolution of 18 µm using Scanco µCT80. Bone volume of distal condyles was determined for each specimen. For histopathologic evaluation, the right knees were trimmed into two equal frontal halves, fixed, decalcified, embedded in paraffin and sectioned. Histologic sections were stained with toluidine blue and examined microscopically. Cartilage matrix damage, bone resorption, subchondral bone sclerosis and osteophyte formation were scored for each sample. All quantitative data were expressed as Mean±SD. Two-way ANOVA and post-hoc Tukey's HSD testing or non-parametric testing were performed using SYSTAT with $P<0.05$ considered significant. At necropsy, the right and left knee joints from all animals were trimmed of muscle and connective tissue and collected into 10% neutral buffered formalin.

Figure 4:
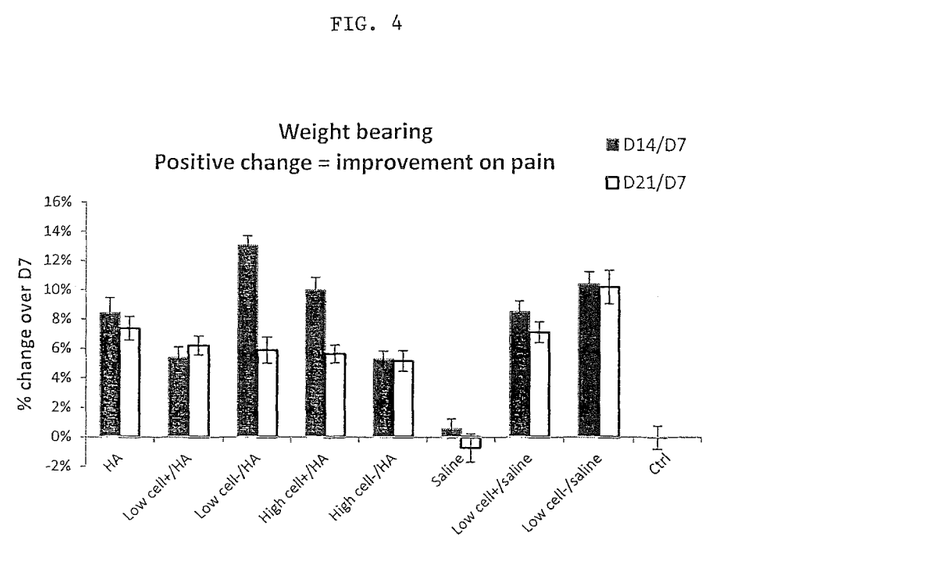
FIG. 4 is a bar graph that illustrates effect on standing pain in rat knees over time following treatment with compositions of the present invention, as compared to controls.

As illustrated in FIG. 4, results for standing pain by Incapacitance were expressed as percent change from Day 7 to normalize the relative effect of each treatment to the rat knee OA. All treatments reduced pain, except the injection of saline alone. IL-1β-primed cells did not seem to further reduce pain as compared to cells which had not been exposed to IL-1β prior to injection.

Figure 5:
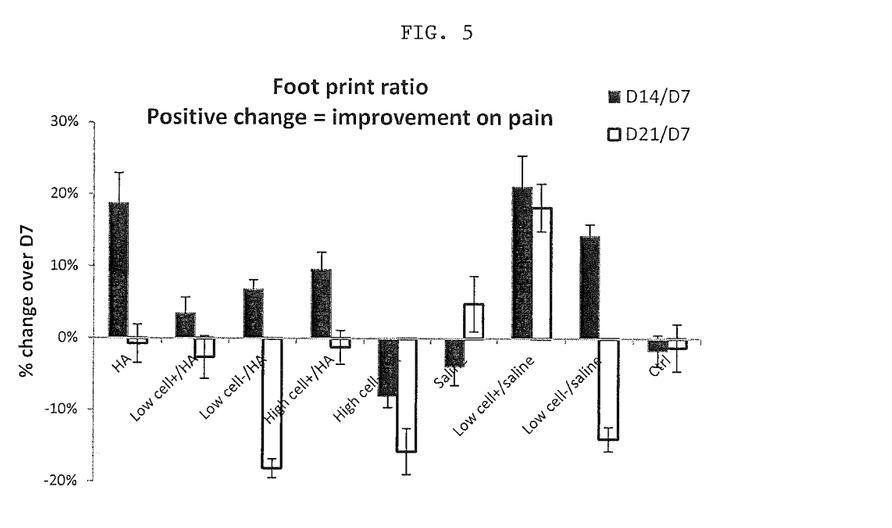
FIG. 5 is a bar graph that illustrates effect on moving pain in rat knees over time following treatment with compositions of the present invention, as compared to controls.

As shown in FIG. 5, results for moving pain on the other hand showed a positive effect on pain reduction when the cells were primed. IL-1β-primed cells showed a prolonged improvement in pain over cells which were not primed, as observed by comparing the Day 21 results. Cells in saline or HyA did not prolong the pain relief observed at Day 14, while primed cells prolonged the pain relief observed at Day 14 to Day 21, or lowered to loss on pain relief observed in the non-primed cell groups.

No significant differences in incidence of synovitis, micro-CT, and histopathology scores were observed between groups.

In conclusion, treatment with stem cells led to sustained relief in both standing and moving joint pain induced by MIA. When cells were primed with IL-1β prior to injection into the joint, either delivered in a saline or HyA carrier, additional pain relief was observed. These results indicate that stem or progenitor cells may be primed prior to their use as therapies to modulate their effect based on the environment to which they may be exposed.

All publications cited in the specification, both patent publications and non-patent publications, are indicative of the level of skill of those skilled in the art to which this invention pertains. Any publication not already incorporated by reference herein is herein incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of treating inflammation in a synovial joint, comprising administering to the synovial joint a composition comprising stem or progenitor cells in an amount effective to enhance recovery, and a pharmaceutically acceptable carrier, wherein prior to the administration, the stem or progenitor cells are exposed to an inflammatory in vitro environment.

2. The method of claim 1, wherein the stem or progenitor cells are autologous progenitor or stem cells.

3. The method of claim 1, wherein the stem or progenitor cells are allogeneic progenitor or stem cells.

4. The method of claim 1, wherein the stem or progenitor cells comprise embryonic stem cells.

5. The method of claim 1, wherein the stem or progenitor cells comprise adult stem cells.

6. The method of claim 5, wherein said adult stem cells comprise placental stem cells, adipose-derived stem cells or bone marrow-derived stem cells.

7. The method of claim 1, wherein the stem or progenitor cells comprise mesenchymal stem cells.

8. The method of claim 1, wherein prior exposure comprises culturing the stem or progenitor cells in autologous or allogeneic synovial fluid isolated from an inflamed joint.

9. The method of claim 1, wherein prior exposure comprises culturing the stem or progenitor cells in a medium comprising at least one pro-inflammatory cytokine selected from the group consisting of interferon-γ, TNF-α and IL-1β; and/or comprising at least one proteolytic enzyme.

10. The method of claim 9, wherein the culturing is conducted for a time period ranging from at least 24 hours to about 2 weeks.

11. The method of claim 10, wherein the at least one pro-inflammatory cytokine is present in the medium at a concentration of about 1 ng/ml to about 50 ng/ml.

12. The method of claim 1, wherein the stem or progenitor cells are transfected with a gene encoding a growth factor, cytokine or extra-cellular matrix compound.

13. The method of claim 1, wherein prior to being administered, the stem or progenitor cells are homed to specifically bind one or more joint tissues, including synovial tissue, joint capsule, articulating cartilage, fibrocartilage (meniscus) tissue, ligament or tendon tissue.

14. The method of claim 1, wherein the pharmaceutically acceptable carrier comprises plasma, optionally enriched with platelets, serum, water for injection, physiological saline, hyaluronan, chemically modified hyaluronan, saline, phosphate buffered saline, chondroitin sulfate, glucosamine, mannosamine, proteoglycan, proteoglycan fragments, chitin, chitosan, or a combination of two or more thereof.

15. The method of claim 1, wherein said composition further comprises a gelling agent, a hydrophilic agent, a surfactant, a lipid, a phospholipid, a surface-active phospholipids, or a combination of two or more thereof.

16. The method of claim 1, wherein said composition further comprises a non-cellular therapeutic agent.

17. The method of claim 16, wherein the non-cellular therapeutic agent comprises a growth factor, a cytokine, a chemokine, a hydrophilic compound, an extracellular matrix compound, or an antimicrobial agent.

18. The method of claim 1, wherein the synovial joint is the knee, hip, shoulder, elbow, ankle, tarsal or metatarsal, wrist, spine, carpal or metacarpal, or temporal mandibular joint.

19. The method of claim 1, wherein the effective amount of the stem or progenitor cells is about $1 \times 10^4$ to about $2 \times 10^8$ cells per administration.

20. The method of claim 1, wherein the synovial joint is osteoarthritic.

* * * * *